US011719607B2

(12) United States Patent
Shuber et al.

(10) Patent No.: US 11,719,607 B2
(45) Date of Patent: *Aug. 8, 2023

(54) METHOD OF PARTIAL LYSIS AND ASSAY

(71) Applicant: Hologic, Inc., Bedford, MA (US)

(72) Inventors: Anthony P. Shuber, Northbridge, MA (US); Steven Hecht, Boston, MA (US); Erin Coffman, Nashua, NH (US); Paul MacLean, Marlborough, MA (US); Howard B. Kaufman, Newton, MA (US)

(73) Assignee: Hologic, Inc., Bedford, MA (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/091,435

(22) Filed: Nov. 6, 2020

(65) Prior Publication Data

US 2021/0072125 A1 Mar. 11, 2021

Related U.S. Application Data

(63) Continuation of application No. 15/730,172, filed on Oct. 11, 2017, now Pat. No. 10,859,475, which is a (Continued)

(51) Int. Cl.
*C12N 15/10* (2006.01)
*C12Q 1/6886* (2018.01)
(Continued)

(52) U.S. Cl.
CPC ............. *G01N 1/30* (2013.01); *C12N 1/066* (2013.01); *C12N 15/101* (2013.01); (Continued)

(58) Field of Classification Search
CPC ...... G01N 1/30; C12N 1/066; C12N 15/1003; C12N 15/101; C12Q 1/6886; C12Q 1/689; C12Q 1/701

See application file for complete search history.

(56) References Cited

U.S. PATENT DOCUMENTS 4,683,195 A   7/1987  Mullis et al.
4,683,202 A   7/1987  Mullis
(Continued)

FOREIGN PATENT DOCUMENTS

JP   2004-501622 A   1/2004
JP   2007-74914 A    3/2007
(Continued)

OTHER PUBLICATIONS

Marinakis et al. Computers in Biology and Medicine. 2009. 39:69-78. (Year: 2009).*

(Continued)

*Primary Examiner* — Joseph G. Dauner
(74) *Attorney, Agent, or Firm* — Brown Rudnick LLP; Adam M. Schoen

(57) ABSTRACT

The present disclosure describes a method of treating a sample comprising cells with a process of partial lysing. Cells are exposed to a process such as bead beating that lyses some cells in the mixture. The process generates a resultant sample mixture that is suitable for both cell morphology screening and genetic screening.

20 Claims, 8 Drawing Sheets

Related U.S. Application Data continuation of application No. 14/856,611, filed on Sep. 17, 2015, now Pat. No. 9,810,610.

(60) Provisional application No. 62/051,672, filed on Sep. 17, 2014.

(51) Int. Cl.
*G01N 1/30* (2006.01)
*C12N 1/06* (2006.01)
*C12Q 1/689* (2018.01)
*C12Q 1/70* (2006.01)

(52) U.S. Cl.
CPC ......... *C12N 15/1003* (2013.01); *C12Q 1/689* (2013.01); *C12Q 1/6886* (2013.01); *C12Q 1/701* (2013.01)

(56) References Cited

U.S. PATENT DOCUMENTS

| | | |
|---|---|---|
| 4,739,044 A | 4/1988 | Stabinsky |
| 4,757,141 A | 7/1988 | Fung et al. |
| 5,750,365 A | 5/1998 | Chiu et al. |
| 5,840,506 A | 11/1998 | Giordano |
| 5,869,717 A | 2/1999 | Frame et al. |
| 5,888,778 A | 3/1999 | Shuber |
| 6,150,517 A | 11/2000 | Hogan et al. |
| 6,177,266 B1 | 1/2001 | Krishnamurthy et al. |
| 6,316,208 B1 | 11/2001 | Roberts et al. |
| 6,531,317 B2 | 3/2003 | Guirguis et al. |
| 6,905,844 B2 | 6/2005 | Kim |
| 7,094,541 B2 | 8/2006 | Brentano et al. |
| 7,153,700 B1 | 12/2006 | Pardee et al. |
| 7,172,863 B1 | 2/2007 | Hogan et al. |
| 7,300,765 B2 | 11/2007 | Patel |
| 7,413,551 B2 | 8/2008 | Decker et al. |
| 8,152,739 B1 | 4/2012 | McCully |
| 2004/0002125 A1 | 1/2004 | Gombrich et al. |
| 2005/0048467 A1 | 3/2005 | Sastry et al. |
| 2005/0260566 A1 | 11/2005 | Fischer et al. |
| 2006/0252077 A1 | 11/2006 | Buzby |
| 2008/0009005 A1 | 1/2008 | Kruk |
| 2008/0044828 A1 | 2/2008 | Kwok |
| 2008/0113340 A1 | 5/2008 | Schlegel |
| 2008/0311570 A1 | 12/2008 | Lai |
| 2009/0023137 A1 | 1/2009 | Van Der Zee et al. |
| 2009/0026082 A1 | 1/2009 | Rothberg et al. |
| 2009/0127589 A1 | 5/2009 | Rothberg et al. |
| 2009/0326414 A1 | 12/2009 | Peltier |
| 2010/0035252 A1 | 2/2010 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0059455 A1 | 3/2011 | Yang et al. |
| 2011/0098462 A1 | 4/2011 | Ehwald et al. |
| 2011/0118626 A1 | 5/2011 | Ragin et al. |
| 2011/0245094 A1 | 10/2011 | Washburn et al. |
| 2012/0259105 A1 | 10/2012 | Chau et al. |

FOREIGN PATENT DOCUMENTS

| | | |
|---|---|---|
| JP | 2012-135317 A | 7/2012 |
| WO | 2005/116256 A2 | 12/2005 |
| WO | 2006/138444 A2 | 12/2006 |
| WO | 2010/056728 A1 | 5/2010 |
| WO | 2011/109705 A2 | 9/2011 |
| WO | 2013/029919 A1 | 3/2013 |
| WO | 2014/029791 A1 | 2/2014 |
| WO | 2016/044510 A1 | 3/2016 |

OTHER PUBLICATIONS

Agrawal et al., 1990, Tetrahedron Letters 31:1543-46.
Australian Examination Report issued in Australian Application No. 2015317692, dated Nov. 27, 2020, 4 pages.
Caruthers, 1985, Science 230:281-85.
Chinese Office Action and English translation issued in Chinese Application No. 201580062378.7, dated Oct. 22, 2020, 11 pages.
Extended European Search Report dated May 4, 2018 for EP 15842335.0 (7 pages).
Giusti et al., 1993, PCR Methods and Application 2:223-27.
Hellman et al., 2009, British Journal of Cancer 100(8):1303-14.
Iftner et al., 2009, "Study Comparing Human Papillomavirus (HPV) Real-Time Multiplex PCR and Hybrid Capture II INNO-LiPA v2 HPV Genotyping PCR Assays," Journal of Clinical Microbiology 47(7):2106-13.
International Search Report dated Dec. 11, 2015, for International Application PCT/US15/50553, filed Sep. 17, 2015 (8 pages).
International Search Report dated Dec. 14, 2015, for International Application PCT/US15/50551, filed Sep. 17, 2015 (7 pages).
Japanese Office Action for Application No. 2017-514822 dated May 30, 2019.
Joos et al., 1997, Analytical Biochemistry 247:96-101.
Kambara et al., 1988, Biotechnology 6:816-21.
Khandjian 1986, Molecular Biology Reports 11:107-15.
Margulies et al., 2005, Nature 437:376-80.
Nelson et al., 1989, Nucleic Acids Research 17:7187-94.
Oroskar et al., 1996, Clinical Chemistry 42:1547-55.
Pollack, 2014, "F.D.A. Panel Recommends Replacement for the Pap Test," New York Times, available at http://www.nytimes.com/2014/03/13/health/an-fda-panel-recommends-a-possible-replacement-for-the-pap-test.html?_r=1, retrieved Sep. 25, 2015.
Sharma et al., 1991, Nucleic Acids Research 19:3019-25.
Smith et al., 1985, Nucleic Acids Research 13:2399-2412.
Smith et al., 1986, Nature 321:674-79.
Smith et al., 1992, Science 253:1122.
Soni et al., 2007, Clinical Chemistry 53:1996-2001.
Sproat et al., 1987, Nucleic Acids Research 15:4837-48.
Taylor et al., 1991, Journal of Physics D: Applied Physics 24:1443.
Zuckerman et al., 1987, Nucleic Acids Research 15:5305-21.

\* cited by examiner

| Condition | Caski concentration (cells/mL) | Sample volume (mL) | Garnet bead concentration (g/20mL) | Mix time |
|---|---|---|---|---|
| A | 100,000 | 20 | 0.5 | 0 (no mix) |
| B | 100,000 | 20 | 0.5 | 5 sec |
| C | 100,000 | 20 | 0.5 | 15 sec |
| D | 100,000 | 20 | 0.5 | 30 sec |
| E | 100,000 | 20 | 0.5 | 1 min |
| F | 100,000 | 20 | 0.5 | 5 min |
| G | 100,000 | 20 | 0.5 | 10 min |
| H | 100,000 | 20 | 0.5 | 20 min |
| I | 100,000 | 20 | 0.5 | 30 min |
| Control 1 | 100,000 | 20 | 0 (no beads) | 0 (no mix) |
| Control 2 | 100,000 | 20 | 0 (no beads) | 1 min |
| Control 3 | 100,000 | 20 | 0 (no beads) | 30 min |

FIG. 5

| Mix time | Average Hemacytometer Count* | Calculated Cell Concentration |
|---|---|---|
| 0 (no mix) | 73 | 91250 |
| 5 sec | 87 | 108750 |
| 15 sec | 91 | 113750 |
| 30 sec | 68 | 85000 |
| 1 min | 40 | 50000 |
| 5 min | N/A (too much debris) | n/a |
| 10 min | N/A (too much debris) | n/a |
| 20 min | N/A (too much debris) | n/a |
| 30 min | N/A (too much debris) | n/a |
| 0 (no mix) | 102 | 127500 |
| 1 min | 68 | 85000 |
| 30 min | 78 | 97500 |

*Counts are an average of 3 separate hemacytometer counts where 8 squares (i.e. 0.8uL volume) were counted.

FIG. 6

METHOD OF PARTIAL LYSIS AND ASSAY

CROSS-REFERENCE TO RELATED APPLICATIONS

This application is a continuation of U.S. Ser. No. 15/730,172, filed on Oct. 11, 2017, which is a continuation of U.S. Ser. No. 14/856,611, which issued on Nov. 7, 2017 as U.S. Pat. No. 9,810,610, which claims the benefit of and priority to U.S. Provisional Application Ser. No. 62/051,672, filed Sep. 17, 2014, the contents of each of which are incorporated by reference herein in their entirety.

FIELD OF THE INVENTION

The invention relates to methods for treating a sample for both cell morphology screening and screening for molecular components.

BACKGROUND

The Papanicolaou (Pap) test is a widely-used method of cervical screening that detects abnormalities in cervical and endometrial cells, including pre-cancerous and cancerous lesions. The Pap test is widely used because it is simple, minimally invasive, and inexpensive. The test generally involves taking a sample of cells from the cervix using a collection device, and assaying the cells for certain diagnostic characteristics that are indicative of the presence of Human Papillomaviruses (HPV). Early detection of cervical abnormalities is essential for effective treatment, and regular Pap screening has reduced the number of annual deaths in the United States by more than 60% since its introduction in 1955 (National Cancer Institute).

To obtain a cervical sample, clinicians generally use a brush or a spatula to collect cells from the cervix and the endocervical canal. The specimen is then either directly smeared onto a glass slide (i.e., conventional "Pap smear"), or collected into a liquid based cytology medium (LBC). With LBC, the collection device is submerged in a preservative medium such as ThinPrep® PreservCyt® Solution available from Hologic, Inc. (Bedford, Mass.) and stirred to release cells into the medium. Exposure to the LBC medium fixes the cells, enabling them to be evaluated for cell morphology. Greater details of useful LBC mediums can be found in U.S. Pat. No. 6,531,317 which is incorporated herein by reference in its entirety.

The current standard of care is to fix a portion of the collected cells on a slide for evaluation of cell morphology. The slides may be prepared by hand ("Pap smear"), however superior results can be obtained with automated systems, such as Hologic's ThinPrep® Pap test combined with the ThinPrep® Imaging System. This methodology is superior to the conventional Pap smear because of improved accuracy and increased disease detection(citation-Surveillance, Epidemiology, and End Results (SEER) Program. SEER Database: Incidence-SEER 9 Regs Public-Use, November 2004 Sub (1973-2002), National Cancer Institute, DCCPS, Surveillance Research Program, Cancer Statistics Branch, released April 2005, based on November 2004 submission). Once the cells are fixed, the sample may be screened for atypical squamous cells, low grade squamous intraepithelial lesions, high grade squamous intraepithelial lesions, squamous cell carcinomas, atypical glandular cells, adenocarcinomas and other cytologic abnormalities. See, e.g., the Bethesda System for Reporting Cervical Cytology.

Recent advances in genetic screening technologies have made it possible to screen for genetic changes indicative of cancer or infection. For example, cervical samples may be collected and screened for molecular diagnostics using a genetic assay, such as hybrid assay, multiplex PCR, or direct sequencing. The sample may be screened against a database of genetic markers to identify a woman's risk of cervical cancer, by typing for HPV-16, HPV-18, HPV-31, HPV-33, HPV-35, HPV-39, HPV-45, HPV-51, HPV-52, HPV-56, HPV-58, HPV-68, HPV-73 or HPV-82. The screening may be based upon DNA, RNA, or some combination thereof. Commercial systems for diagnostic screening for HPV are available from Hologic, Inc., e.g., Cervista® HPV or APTIMA® HPV assays.

While the standard of care for cervical screening in the United States is still the Pap test, the U.S. Food and Drug Administration recently cleared the way for genetic testing alone to be used to screen women for cervical cancer. However, groups such as the American Medical Women's Association have expressed concern that genetic testing alone without concurrent morphology screening will result in too many women receiving treatment when those women are merely carriers of HPV and don't have any immediate risk of developing cervical cancer. See "FDA approves Roche Genetic Test as an Alternative to Pap Smear for Cervical Cancer Screening," Associated Press, Apr. 24, 2014, incorporated by reference herein in its entirety.

SUMMARY

The present disclosure describes a method of treating a sample with a process of partial lysing, which generates a resultant sample mixture that is suitable for both cell morphology screening and screening for molecular components, such as nucleic acids, pathogens, proteins, and other markers of disease. In some instances, the nucleic acids may be sequenced and compared to genetic markers for disease. In a preferred embodiment, the method comprises mechanically shearing cells in the sample by bead beating, i.e. shaking the sample together with a multitude of beads. The rapid motion of the beads shreds cells. The method involves controlling the degree of lysis, thereby retaining a sufficient number of whole cells in the sample to be observed for cell morphology. After the partial lysis process, cellular structures in the sample are observed by a user, either alone or in conjunction with an automated system such as the Thin Prep® Pap test combined with the ThinPrep® Imaging System, and the sample is also screened for genetic markers such as high-risk HPV types. Surprisingly, the presence of beads in the mixture does not interfere with cytology measurements, e.g. the function of the ThinPrep® processor or Imaging System, nor does it interfere with cellular presentation or visual analysis of the slides.

The method is generally applicable to combinations of cytology and molecular diagnostics. In particular, the method is useful for cervical screening, where a combination of cytology and genetic screening present a more complete picture of cervical health. For example, a first portion of the partially lysed sample can be mounted on a slide and observed for atypical cells and cytologic abnormalities. A second portion of the partially lysed sample can be screened for genetic markers known to correlate with a risk of cervical cancer, e.g., the presence of HPV.

The partial lysing method can comprise mechanical shearing, detergent lysing, osmotic lysing or other methods known in the art, and the chosen technique is adapted to avoid lysing substantially all of the cells in the sample.

Whereas the state of the art cytology techniques teach careful attention to maintaining structural integrity of a sample, the present disclosure recites a method where the same sample, i.e., a partially lysed sample, is suitable for both cytology and molecular diagnostics. This method streamlines the diagnostic process for protocols that require both types of screening assays, such as cervical screening. The process is streamlined because there is no need for double collection. Having only a single point of collection reduces the prevalence of cross-contamination in sensitive testing settings. Also, in contrast with other molecular diagnostic protocols, the present disclosure provides a method whereby the molecular sample is not destroyed in the diagnostic process. The method also allows the simultaneous assay of cell morphology and genetic markers from the same cellular sample.

BRIEF DESCRIPTION OF THE DRAWINGS

FIG. 5 shows a sample table describing a test for refining a partial lysis bead beating protocol.

FIG. 6 shows a table of cell concentration after various durations of bead beating.

DETAILED DESCRIPTION

The present disclosure describes a method of treating a sample with a process of partial lysing, which generates a resultant sample mixture that is suitable for both cell morphology screening and molecular diagnostics. Whereas the state of the art cytology techniques teach careful attention to maintaining structural integrity of a sample, the present disclosure recites a method where the same sample is partially lysed to be suitable for both cytology and molecular diagnostics. This method streamlines the diagnostic process for protocols that require both cytology and genetic screening for thorough examination, such as in cervical screening. Unlike other methods that teach partitioning a sample before lysing (see, e.g., Iftner et al., "Study comparing human papillomavirus (HPV) real-time multiplex PCR and Hybrid Capture II INNO-LiPA v2 HPV genotyping PCR assays," J. Clin. Microbiol. 47(7):2106-13, Jul. 2009), the disclosed method yields satisfactory results for both cytologic analysis and molecular diagnostics, while requiring the use of only one sample.

The invention provides a useful method for cervical screening, for example, because a first portion of the partially lysed sample can be mounted on a slide and observed for atypical cells and cytologic abnormalities, and a second portion of the partially lysed sample can be screened for molecular components, e.g., genetic markers known to correlate with a risk of disease, e.g., cervical cancer. The molecular components may be any acellular component that might be found in a biological sample, such as cell-free DNA, degraded proteins, viruses, fungi, or other chemical marker. The molecular components may also include portions of cells, or cellular substructures, such as chromosomes, proteins, or enzymes. In preferred embodiments, the molecular components are nucleic acids, such as DNA or RNA, such as mRNA, or rRNA.

Figure 1:
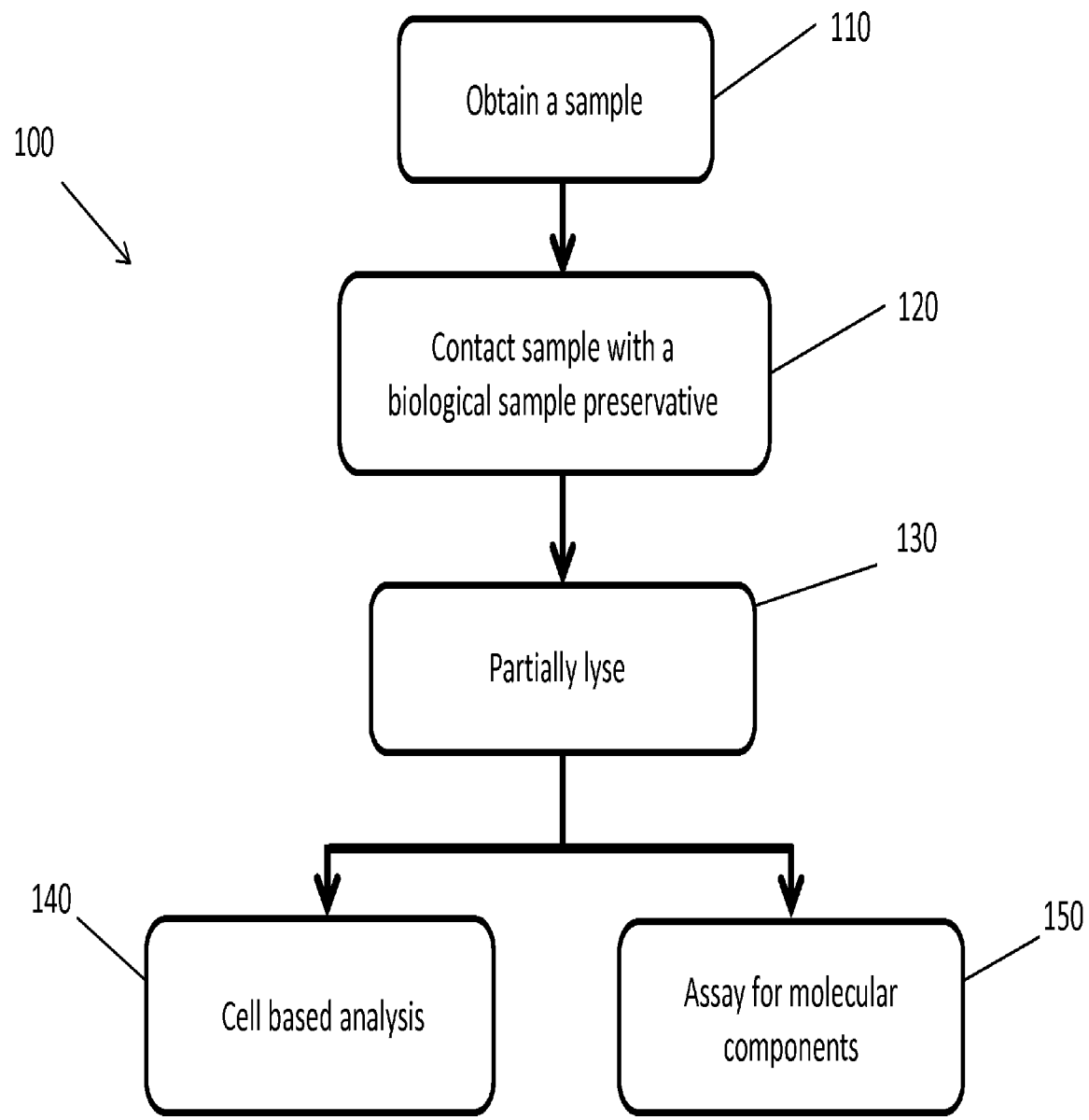
FIG. 1 shows a workflow for screening a sample using a partial lysis method.

FIG. 1 shows a workflow 100 for screening a sample using a partial lysis method. A first step 110 comprises obtaining a sample. The sample can be any biological sample, including a cellular or body fluid sample comprising cells. The sample can be a cervical sample, a buccal sample, a nasal sample, a blood sample, an amniotic fluid sample or other biological materials. The sample can be collected with a brush, a spatula, a swab, a syringe or other apparatuses known in the art. In step 120 the sample is contacted with a biological sample preservative such as PreservCyt® solution to create a preserved biological sample. The biological sample preservative can comprise an alcohol, such as methanol, ethanol or isopropanol; a buffer such as Tris or PBS; a solution comprising formaldehyde; or a detergent such as Tween-20 or Triton X-100. The biological sample preservative can serve to fix cells in the preserved biological sample or otherwise prepare them for cell based analysis.

The preserved biological sample is subjected to a partial lysing process in step 130. Partial lysing yields a mixture comprising at least 10% intact cells. In some embodiments, the mixture comprises at least 20%, 30%, 40%, 50%, 60%, 70%, 80%, 90% or 95% intact cells. Partial lysing can comprise mechanical shearing, detergent lysing, osmotic lysing, chemical denaturing, centrifuging, sonicating, freeze-thawing or other lysis techniques known in the art. Mechanical shearing includes syringe shearing, bead beating, other techniques known in the art or any combination thereof. Whichever lysis technique is chosen is adapted to avoid lysing substantially all of the cells in the preserved biological sample. Methods of the invention involve controlling the degree of lysis to a predetermined level, thereby retaining a sufficient number of whole cells in the mixture to be observed for cell morphology.

In a preferred embodiment, the method comprises mechanically shearing cells in the preserved biological sample by bead beating, i.e. shaking the preserved biological sample together with a multitude of beads, such as the beads sold by MO-BIO Laboratories, Inc. (Carlsbad, Calif.). Shaking cells and beads together in a liquid medium is known to lyse cells. The beads can be made of glass, ceramic, metal, garnet or other materials known in the art. The bead diameter can be smaller than or equal to 0.1 mm, 0.15 mm, 0.25 mm, 0.5 mm, 0.7 mm, 1.4 mm, 2.38 mm, 2.8 mm or larger. The shaking can comprise manually shaking, using an orbital shaker, using a vortex mixer or any other technique known in the art. The duration of shaking may be less than 1 second, 2 seconds, 5 seconds, 10 seconds, 15 seconds, 20 seconds, 30 seconds, 45 seconds, 1 minute, 2 minutes, 5 minutes, 10 minutes, 15 minutes, 20 minutes, 30 minutes or longer.

In another embodiment, the method comprises partially lysing cells in the preserved biological sample by syringe shearing. The cells in solution are pumped through a syringe needle, such as those reusable stainless steel needles pictured in FIG. 4 from McMaster-Carr (Robbinsville, N.J.). The needle length can be less than 10 mm, less than 20 mm, less than 30 mm, less than 50 mm, less than 80 mm, less than 100 mm, less than 200 mm or greater. The bore size of the needle can be 152 µm, 203 µm, 254 µm, 406 µm, 610 µm, 686 µm or greater. The cells in solution can be pumped through the needle manually or with the use of a pump motor driven by an external power supply. The syringe may be pumped with a single unidirectional stroke or with multiple back-and-forth strokes.

After the partial lysis process, a portion of the mixture is used for cell based analysis in step 140, and another portion of the mixture is assayed for molecular components in step 150. Cell based analysis (step 140) may be done by a clinician mounting cells on a slide and observing them under a microscope. When screening for cervical cancer, the cells are screened for squamous cell abnormalities or glandular cell abnormalities. The mixture may instead be run through an automated imaging machine such as the ThinPrep® Pap test combined with the ThinPrep® Imaging System to detect abnormalities. In embodiments where bead beating is used to partially lyse cells, the beads do not have to be removed prior to imaging. Surprisingly, the presence of beads in the mixture does not interfere with the function of the ThinPrep® processor or Imager, nor does it interfere with visual analysis of the slides. Slides prepared from bead beating of certain durations and syringe shearing show little to no cellular debris or degradation and are suitable for cell based analysis.

To use the ThinPrep® system, a user places a vial containing cells with PreservCyt® Solution into the ThinPrep® processor, along with a ThinPrep® slide and a TransCyt® filter. The Imager homogenizes the mixture by spinning, and the filter collects cells with the aid of gentle aspiration. The filter then contacts the slide to transfer a thin layer of cells to the slide. The slide is then contacted with a fixative agent, after which it can be stained and coverslipped.

For the cell based analysis, the ThinPrep® Imager scans every cell and cell cluster on the slide to measure DNA content. The Imager identifies the largest and darkest nuclei on the slide and highlights them for review by a cytotechnologist, helping to focus their analysis. This "dual review" screening process by the Imager and a cytotechnologist has been proven to increase disease detection over manual review alone, and reduces false negatives by 39% (see How Dual Screening Works, http://www.thinprep.com/hcp/imaging_system/dual_review_screening.html). Slides prepared from bead beating of certain durations and syringe shearing show little to no cellular debris or degradation and are suitable for observing cellular structures.

Assaying for molecular components (step 150) may comprise centrifuging all or a portion of the mixture. Centrifuging can be performed at radial forces of 10 g, 50 g, 100 g, 200 g, 300 g, 600 g, 1000 g, 2000 g or greater. The duration of centrifugation may be 10 seconds, 30 seconds, 1 minute, 2 minutes, 5 minutes, 10 minutes or more. Step 150 may further comprise drawing off an aliquot of supernatant to be screened. Step 150 may further comprise detecting nucleic acids, quantifying nucleic acids, identifying nucleic acids, sequencing or the like.

Genetic screening can be performed by commercial systems such as Cervista® HPV or APTIMA® HPV from Hologic. Cervista® HPV detects individual base pair changes associated with high-risk HPV strains using signal amplification and fluorescence detection. Cervista® HPV uses proprietary Invader™ chemistry, consisting of a primary reaction and a secondary reaction. In the primary reaction, an Invader™ probe binds with the target area of the viral DNA and generates an overlapping structure. The flap of this structure is then cleaved with a proprietary Cleavase® enzyme. Multiple flaps are created through this process, which will bind to a universal fluorescently labeled hairpin structure in the secondary reaction. In the secondary reaction, the cleaved flaps created in the primary reaction function as a probe, binding with complementary sequences of the hairpin structure, also known as a Fluorescence Resonance Energy Transfer (FRET) cassette. The secondary reaction utilizes the combination of cleaved flaps and FRET cassettes to create fluorescence-based signal amplification. The fluorescent signal is then measured by a fluorometer to confirm the presence (or absence) of a high-risk HPV strain. Concurrently in a parallel reaction, the Cervista® HPV HR test's unique internal control generates a red fluorescent signal when adequate DNA is present in the sample for testing. A green fluorescent signal indicates the presence of high-risk HPV types. The APTIMA® HPV system from Hologic targets mRNA to identify 14 high-risk HPV types. The APTIMA system includes mRNA target capture, target amplification, and detection of amplification products. A similar APTIMA test can also be used to identify ribosomal RNA (rRNA) from *Chlamydia trachomatis* or *Neisseria gonorrhoeae* to aid in the diagnosis of chlamydial or gonococcal urogenital infections. Additional information regarding APTIMA assays is described in U.S. Pat. Nos. 5,750,365, 6,150,517, 7,094,541 and 7,172,863 all of which are incorporated by reference herein.

In an embodiment where the method is used for cervical screening or other genetic screening, step 150 additionally comprises comparing an identified nucleic acid to a database of known markers to determine if the subject carries a known marker. The database of known markers can comprise markers used to identify a woman's risk for cervical cancer, including HPV-6, HPV-11, HPV-16, HPV-18, HPV-31, HPV-33, HPV-35, HPV-39, HPV-45, HPV-51, HPV-52, or HPV-68 (American Cancer Society, Human Papilloma Virus (HPV), Cancer, HPV Testing, and HPV Vaccines: Frequently Asked Questions (Oct. 22, 2013). Other nucleic acid biomarkers may be used, included those described below. Methods of nucleic acid amplification, detection and sequencing described below may also be used in the embodiment of the method depicted in FIG. 1.

Figure 2:
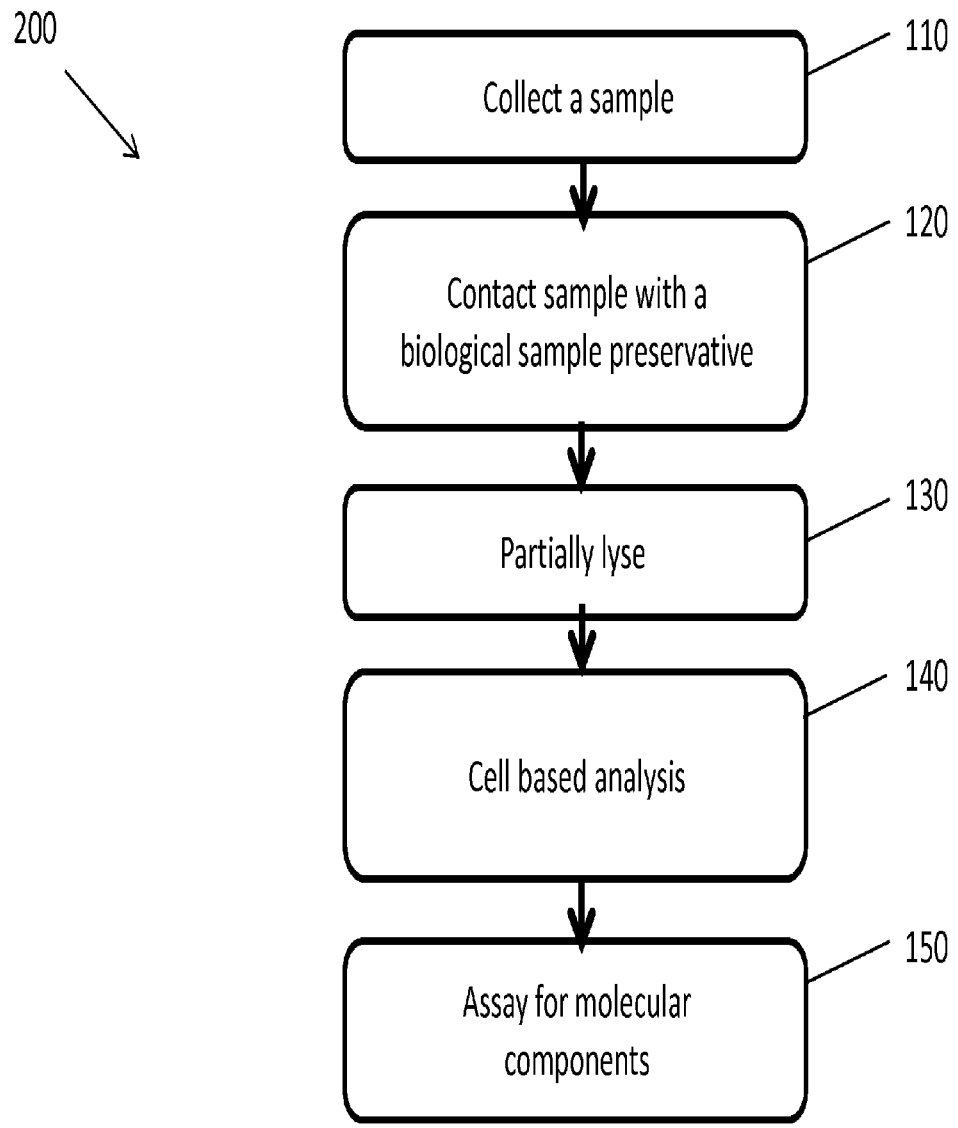
FIG. 2 shows a workflow for screening a sample using a partial lysis method.

FIG. 2 shows a workflow 200 for screening a sample using a partial lysis method. A first step 110 comprises collecting a sample. The sample can be any biological sample, including a cellular or body fluid sample comprising cells. The sample can be a cervical sample, a buccal sample, a nasal sample, a blood sample, an amniotic fluid sample or other biological materials. The sample can be collected with a brush, a spatula, a swab, a syringe or other apparatuses known in the art. In step 120 the sample is contacted with a biological sample preservative such as PreservCyt® solution to create a preserved biological sample. The biological sample preservative can comprise an alcohol, such as methanol, ethanol or isopropanol; a buffer such as Tris or PBS; or a detergent such as Tween-20 or Triton X-100. The biological sample preservative can serve to fix cells in the preserved biological sample or otherwise prepare them for cell based analysis.

The preserved biological sample is subjected to a partial lysing process in step 130. Partial lysing yields a mixture comprising least 10% intact cells. In some embodiments, the mixture comprises at least 20%, 30%, 40%, 50%, 60%, 70%, 80%, 90% or 95% intact cells. Partial lysing can comprise mechanical shearing, detergent lysing, osmotic lysing, chemical denaturing, centrifuging, sonicating, freeze-thawing or other lysis techniques known in the art. Mechanical shearing includes syringe shearing, bead beating, other techniques known in the art or any combination thereof. Whichever lysis technique is chosen is adapted to avoid lysing substantially all of the cells in the preserved biological sample. The method of this disclosure involves controlling the degree of lysis, thereby retaining a sufficient number of whole cells in the mixture to be observed for cell morphology.

In a preferred embodiment, the method comprises mechanically shearing cells in the preserved biological sample by bead beating, i.e. shaking the preserved biological sample together with a multitude of beads, such as the beads sold by MO-BIO Laboratories, Inc. (Carlsbad, Calif.). Shaking cells and beads together in a liquid medium is known to lyse cells. The beads can be made of glass, ceramic, metal, garnet or other materials known in the art. The bead diameter can be smaller than or equal to 0.1 mm, 0.15 mm, 0.25 mm, 0.5 mm, 0.7 mm, 1.4 mm, 2.38 mm, 2.8 mm or larger. The shaking can comprise manually shaking, using an orbital shaker, using a vortex mixer or any other technique known in the art. The duration of shaking may be less than 1 second, 2 seconds, 5 seconds, 10 seconds, 15 seconds, 20 seconds, 30 seconds, 45 seconds, 1 minute, 2 minutes, 5 minutes, 10 minutes, 15 minutes, 20 minutes, 30 minutes or longer.

In another embodiment, the method comprises partially lysing cells in the preserved biological sample by syringe shearing. The cells in solution are pumped through a syringe needle, such as those reusable stainless steel needles pictured in FIG. 4 from McMaster-Carr (Robbinsville, N.J.). The needle length can be less than 10 mm, less than 20 mm, less than 30 mm, less than 50 mm, less than 80 mm, less than 100 mm, less than 200 mm or greater. The bore size of the needle can be 152 µm, 203 µm, 254 µm, 406 µm, 610 µm, 686 µm or greater. The cells in solution can be pumped through the needle manually or with the use of a pump motor driven by an external power supply. The syringe may be pumped with a single unidirectional stroke or with multiple back-and-forth strokes.

After the partial lysis process, the mixture is used for cell based analysis in step 140. Cell based analysis (step 140) may be done by a clinician mounting cells on a slide and observing them under a microscope. When screening for cervical cancer, the cells are screened for squamous cell abnormalities or glandular cell abnormalities. The mixture may instead be run through an automated imaging machine such as the ThinPrep® Imaging System to detect abnormalities. In embodiments where bead beating is used to partially lyse cells, the beads do not have to be removed prior to imaging. Surprisingly, the presence of beads in the mixture does not interfere with the function of the ThinPrep® processor or ThinPrep® Imager, nor does it interfere with visual analysis of the slides. Details of the ThinPrep® system are outlined above. Slides prepared from bead beating of certain durations and syringe shearing show little to no cellular debris or degradation and are suitable for cell based analysis.

The cells are assayed for cellular components in step 150. Assaying for cellular components 150 may comprise centrifuging the mixture. Centrifuging can be performed at radial forces of 10 g, 50 g, 100 g, 200 g, 300 g, 600 g, 1000 g, 2000 g or greater. The duration of centrifugation may be 10 seconds, 30 seconds, 1 minute, 2 minutes, 5 minutes, 10 minutes or more. Step 150 may further comprise drawing off an aliquot of supernatant to be screened. Step 150 may further comprise detecting nucleic acids, quantifying nucleic acids, identifying nucleic acids, sequencing or the like. Genetic screening can be performed by commercial devices such as Cervista® HPV or APTIVA® HPV from Hologic, details of which are described above.

In an embodiment where the method is used for cervical screening or other genetic screening, step 150 additionally comprises comparing an identified nucleic acid to a database of known markers to determine if the subject carries a known marker. The database of known markers can comprise markers correlated with an elevated risk of cancer, such as markers used to identify a woman's risk of cervical cancer, including HPV-6, HPV-11, HPV-16, HPV-18, HPV-31, HPV-33, HPV-35, HPV-39, HPV-45, HPV-51, HPV-52, or HPV-68 (American Cancer Society, Human Papilloma Virus (HPV), Cancer, HPV Testing, and HPV Vaccines: Frequently Asked Questions (Oct. 22, 2013). Other nucleic acid biomarkers may be used, included those described below. Methods of nucleic acid amplification, detection and sequencing described below may also be used in the embodiment of the method depicted in FIG. 2.

Figure 3:
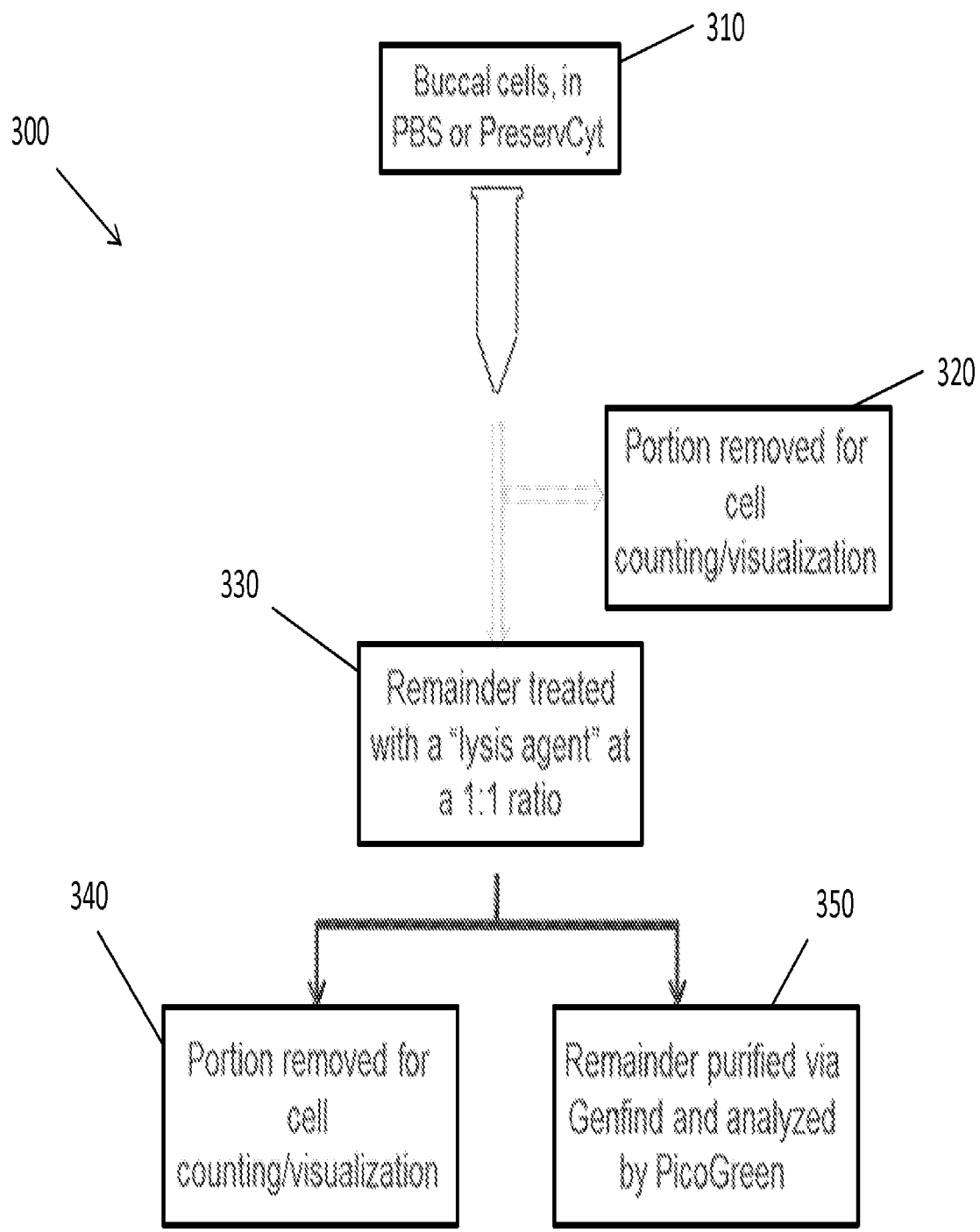
FIG. 3 shows a flowchart of an experimental design for comparing cell counting and visualization from before and after the partial lysis method.

FIG. 3 shows a flowchart of an experimental design 300 for comparing cell counting and visualization from before and after the partial lysis method. The experimental design 300 begins with a sample of buccal cells in a liquid medium 310. The liquid medium can be PBS, PreservCyt® solution or any other media described above. A portion of the sample is removed and counted or visualized 320. Cell counting techniques that can be used with the disclosed method include spectrophotometry, hemocytometry, flow cytometry or the like. Cells can be visualized by mounting and observing under a microscope or with an imaging system such as the ThinPrep® system. The remainder of the sample is partially lysed 330 to generate a partially lysed mixture. The mixture contains lysed cells. Lysed cells comprise cellular components and fragments thereof. The mixture also contains molecular components of the cell, which include nucleic acids, proteins, organelles, and other sub-cellular structures. Molecular components also include components of pathogens present in the biological sample. Such pathogens include bacteria, viruses, yeast, and the like. Specifically, pathogens may be associated with diseases including chlamydia, gonorrhea, trichomoniasis, and candidiasis. The partial lysis step 330 can comprise any of the partial lysis techniques described above. Aliquots of the partially lysed mixture are removed for cell counting and visualization 340, on the one hand, and purification and molecular analysis 350, on the other hand. The results of the cell counting and visualization step 320 can be compared with the results of the cell counting and visualization step 340 to determine the effect of the partial lysis step 330. To the extent that cells in step 340 are too degraded for adequate counting and visualization, or to the extent that the sample has been insufficiently lysed to conduct molecular analysis in step 350, the partial lysis step 330 can be adjusted accordingly. In embodiments wherein the partial lysis step 330 comprises bead beating, possible adjustments include altering the number of beads, the size of beads, the material of beads, the duration of mixing or vortexing, or other quantitative or qualitative alterations to the lysis procedure, as described above. In embodiments wherein the partial lysis step 330 comprises syringe shearing, possible adjustments include altering the length or diameter of the syringe or changing the pressure applied to expel the cells through the syringe. In embodiments where the partial lysis step 330 comprises detergent lysis, osmotic lysis or chemical denaturing, possible adjustments include altering the concentrations of reagents, or substituting reagents.

Figure 4:
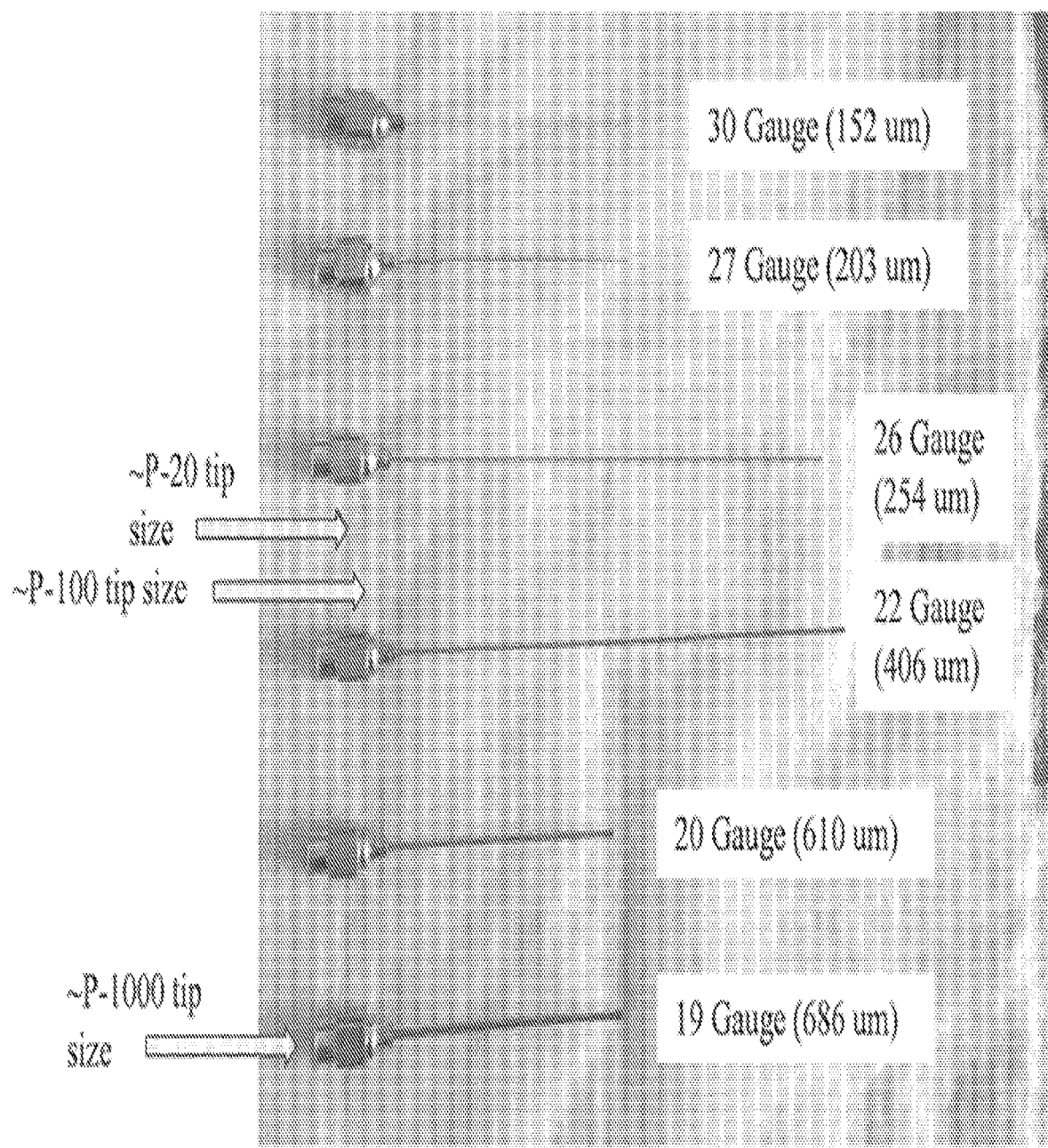
FIG. 4 shows a variety of needles suitable for use with a mechanical shearing method.

FIG. 4 shows a variety of reusable stainless steel needles from McMaster-Carr (Robbinsville, N.J.) suitable for use with a mechanical shearing method comprising syringe shearing. The needles vary in length and bore size. The needle length can be less than 10 mm, less than 20 mm, less than 30 mm, less than 50 mm, less than 80 mm, less than 100 mm, less than 200 mm or greater. The bore size of the needle can be 152 µm, 203 µm, 254 µm, 406 µm, 610 µm, 686 µm or greater. To implement the syringe shearing technique, cells in solution can be pumped through a needle manually or with the use of a pump motor driven by an external power supply. The syringe may be pumped with a single unidirectional stroke or with multiple back-and-forth strokes.

FIG. 5 shows a sample table describing a test for refining a partial lysis bead beating protocol. Cell-line based Thin-Prep® specimens were created using culture CaSki cells at a concentration of 100,000 cells/mL. Garnet beads (MO-BIO P/N 13123-05) were added to each 20 mL sample, and samples were subject to varying mix times on a vortexer. Controls were also prepared, in which no beads were added to the CaSki samples. This table helps the user determine optimal mixing time for a bead beating protocol. Other tables can be made with variations to other conditions in the protocol to refine the partial lysis method. For example, an investigator could change the bead material, the bead size, the bead concentration or the bead volume. Similar tables can be constructed for other partial lysis protocols, including a syringe shearing protocol. For a table for testing a syringe shearing protocol, variables can include needle length, bore size, pump pressure and time.

FIG. 6 shows a table of cell concentration after various durations of bead beating from the experimental method of FIG. 5. A 100 µl aliquot was removed from each sample before and after lysis, and cell concentrations were quantified. Cell counts before lysis were an average of 84,000 cells/mL. Cell counts after lysis are shown in FIG. 6. For the increased lysis times, counting cells were not able to be counted because of increased levels of cellular debris. This suggests that under some conditions mixing for longer than 5 minutes may not achieve a usable result.

Figure 7:
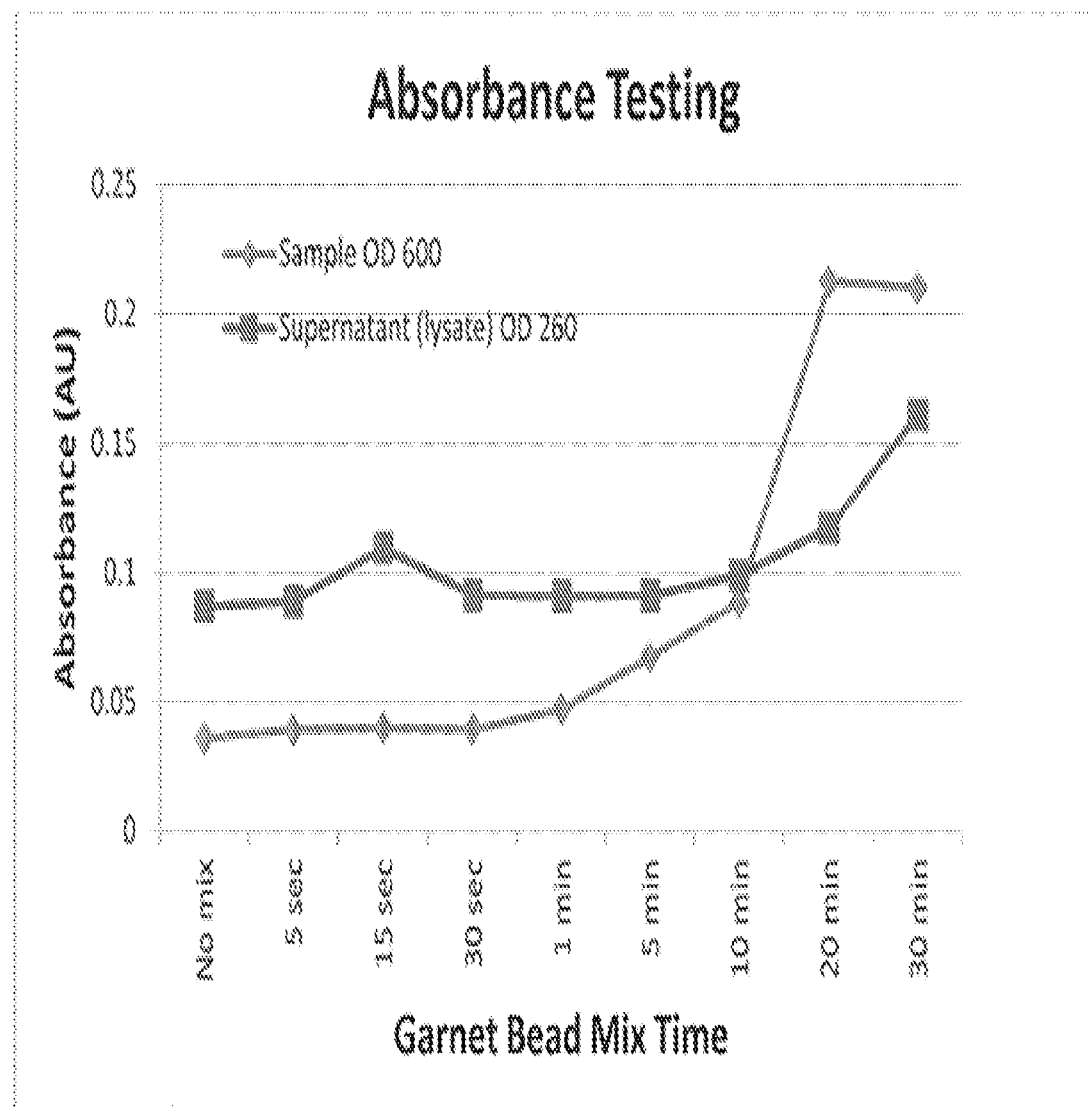
FIG. 7 shows absorbance results of various tests of the bead beating method.

FIG. 7 shows absorbance results after various durations of bead beating from the experimental method of FIG. 5. Post-lysis cells were centrifuged at 600 g for 5 minutes, and 0.1 mL of supernatant was removed for absorbance readings. Absorbance increases with mix times. This indicates that under some conditions excessive lysis may decrease visibility of structures in the sample.

Nucleic acids may be obtained by methods known in the art. Generally, nucleic acids can be extracted from the partially lysed sample by a variety of techniques such as those described by Maniatis, et al., Molecular Cloning: A Laboratory Manual, Cold Spring Harbor, N.Y., pp. 280-281, (1982), the contents of which is incorporated by reference herein in its entirety.

In an embodiment where the method is used for cervical screening or other genetic screening, step 150 additionally comprises comparing an identified nucleic acid to a database of known markers to determine if the subject carries a known marker. The database of known markers can comprise markers correlated with an elevated risk of cancer, such as markers associated with a woman's risk for developing cervical cancer, including HPV-6, HPV-11, HPV-16, HPV-18, HPV-31, HPV-33, HPV-35, HPV-39, HPV-45, HPV-51, HPV-52, or HPV-68 (American Cancer Society, Human Papilloma Virus (HPV), Cancer, HPV Testing, and HPV Vaccines: Frequently Asked Questions (Oct. 22, 2013)). Biomarkers associated with development of cervical cancer are also shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). The contents of each of the articles, patents, and patent applications are incorporated by reference herein in their entirety. Exemplary biomarkers that have been associated with cervical cancer include: SC6; SIX1; human cervical cancer 2 protooncogene (HCCR-2); p27; virus oncogene E6; virus oncogene E7; p16INK4A; Mcm proteins (such as Mcm5); Cdc proteins; topoisomerase 2 alpha; PCNA; Ki-67; Cyclin E; p-53; PAI1; DAP-kinase; ESR1; APC; TIMP-3; RAR-β; CALCA; TSLC1; TIMP-2; DcR1; CUDR; DcR2; BRCA1; p15; MSH2; Rassf1A; MLH1; MGMT; SOX1; PAX1; LMX1A; NKX6-1; WT1; ONECUT1; SPAG9; and Rb (retinoblastoma) proteins.

Biomarkers associated with development of vaginal cancer are shown in Giordano (U.S. Pat. No. 5,840,506), Kruk (US 2008/0009005), Hellman et al. (Br J Cancer. 100(8): 1303-1314, 2009). The contents of each of the articles, patents, and patent applications are incorporated by reference herein in their entirety. Exemplary biomarkers that have been associated with vaginal cancer include: pRb2/p130 and Bcl-2.

The invention is not limited to cancer screening. It may be used to screen for biomarkers of a variety of traits. Nucleic acid biomarkers are often associated with nucleic acid mutations, which include additions, deletions, insertions, rearrangements, inversions, transitions, transversions, frameshift mutations, nonsense mutations, missense mutations, single nucleotide polymorphisms (SNP) and substitutions of two or more nucleotides within a sequence but not to the extent of large chromosomal sequence changes. SNPs are a type of genomic subtle sequence change that occurs when a single nucleotide replaces another within the sequence. Alterations in chromosome numbers include additions, deletions, inversions, translocations, copy number variations, and substitutions of chromosomes within a sequence. These nucleic acid mutations in biomarkers may also be indicative of cancer.

Nucleic acid biomarkers may be assayed or detected by any method known in the art for use in a single multi-analyte screening assay. Methods of the invention provide for conducting at least one detection assay on the plurality of biomarkers to look for any one of the characteristics indicative of cancer described above. Any combination of biomarkers or characteristics can be assayed using the same sequencing platform or different sequencing platforms. Accordingly, more than one detection technique can be conducted on the plurality of biomarkers to look for any variety of characteristics for the single multi-analyte screening assay. For example, one detection technique can be chosen because it is particularly suitable for detection of a particular biomarker and another detection technique can be chosen because it is particular suitable for detecting a particular characteristic.

Probes suitable for use in the present invention include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. Probes can be single stranded or double stranded. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA.

The length of the nucleotide probe is not critical, as long as the probes are capable of hybridizing to the target nucleic acid and nucleic acid ligand. In fact, probes may be of any length. For example, probes may be as few as 5 nucleotides, or as much as 5000 nucleotides. Exemplary probes are 5-mers, 10-mers, 15-mers, 20-mers, 25-mers, 50-mers, 100-mers, 200-mers, 500-mers, 1000-mers, 3000-mers, or 5000-mers. Methods for determining an optimal probe length are known in the art. See, e.g., Shuber, U.S. Pat. No. 5,888,778, hereby incorporated by reference in its entirety.

Probes used for detection may include a detectable label, such as a radiolabel, fluorescent label, or enzymatic label. See for example Lancaster et al., U.S. Pat. No. 5,869,717, hereby incorporated by reference. In certain embodiments, the probe is fluorescently labeled. Fluorescently labeled nucleotides may be produced by various techniques, such as those described in Kambara et al., Bio/Technol., 6:816-21, (1988); Smith et al., Nucl. Acid Res., 13:2399-2412, (1985); and Smith et al., Nature, 321: 674-679, (1986), the contents of each of which are herein incorporated by reference in their entirety. The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach, IRL Press, Oxford, (1991); Zuckerman et al., Polynucleotides Res., 15: 5305-5321, (1987); Sharma et al., Polynucleotides Res., 19:3019, (1991); Giusti et al., PCR Methods and Applications, 2:223-227, (1993); Fung et al. (U.S. Pat. No. 4,757,141); Stabinsky (U.S. Pat. No. 4,739,044); Agrawal et al., Tetrahedron Letters, 31:1543-1546, (1990); Sproat et al., Polynucleotides Res., 15:4837, (1987); and Nelson et al., Polynucleotides Res., 17:7187-7194, (1989), the contents of each of which are herein incorporated by reference in their entirety. Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

The detectable label attached to the probe may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; alexa; fluorescien; conjugated multi-dyes; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.™. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Labels other than fluorescent labels are contemplated by the invention, including other optically-detectable labels.

In certain embodiments, nucleic acid is detected using sequencing. Sequencing-by-synthesis is a common technique used in next generation procedures and works well with the instant invention. However, other sequencing methods can be used, including sequence-by-ligation, sequencing-by-hybridization, gel-based techniques and others. In general, sequencing involves hybridizing a primer to a template to form a template/primer duplex, contacting the duplex with a polymerase in the presence of a detectably-labeled nucleotides under conditions that permit the polymerase to add nucleotides to the primer in a template-dependent manner. Signal from the detectable label is then used to identify the incorporated base and the steps are sequentially repeated in order to determine the linear order of nucleotides in the template. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes. Numerous techniques are known for detecting sequences and some are exemplified below. However, the exact means for detecting and compiling sequence data does not affect the function of the invention described herein.

In a preferred embodiment, nucleic acids are detected using single molecule sequencing. An example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured.

Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a single molecule sequencing technique suitable for use in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H+), which signal detected and recorded in a sequencing instrument. The signal strength is proportional to the number of nucleotides incorporated. User guides describe in detail the Ion Torrent protocol(s) that are suitable for use in methods of the invention, such as Life Technologies' literature entitled "Ion Sequencing Kit for User Guide v. 2.0" for use with their sequencing platform the Personal Genome Machine™ (PCG).

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

In an instance where there is insufficient DNA for a complex assay, e.g. next generation sequencing, a common technique used to increase the amount of nucleic acid in a sample is to perform PCR on the sample prior to performing an assay that detects the nucleic acids in the sample. PCR refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target nucleic acid sequence and nucleic acid ligand includes introducing an excess of oligonucleotide primers that bind the nucleic acid and the nucleic acid ligand, followed by a precise sequence of thermal cycling in the presence of a DNA polymerase. The primers are complementary to their respective strands of the target nucleic acid and nucleic acid ligand. The PCR process amplifies the DNA in the sample and produces an amount of DNA sufficient for detection by standard assays known in the art, such as Southern blots or sequencing. Other variations on PCR include nested polymerase chain reaction, polymerase chain reaction-single strand conformation polymorphism, ligase chain reaction, strand displacement amplification and restriction fragments length polymorphism.

With PCR, it is possible to amplify a single copy of a specific target sequence in genomic DNA to a level that can be detected by several different methodologies (e.g., staining, hybridization with a labeled probe, incorporation of biotinylated primers followed by avidin-enzyme conjugate detection, incorporation of 32P-labeled deoxynucleotide triphosphates, such as dCTP or dATP, into the amplified segment). In one embodiment of the invention, the target nucleic acid and nucleic acid ligand can be detected using detectably labeled probes. Nucleic acid probe design and methods of synthesizing oligonucleotide probes are known in the art. See, e.g., Sambrook et al., DNA microarray: A Molecular Cloning Manual, Cold Spring Harbor, N.Y., (2003) or Maniatis, et al., Molecular Cloning: A Laboratory Manual, Cold Spring Harbor, N.Y., (1982), the contents of each of which are herein incorporated by reference herein in their entirety. Sambrook et al., Molecular Cloning: A Laboratory Manual (2nd Ed.), Vols. 1-3, Cold Spring Harbor Laboratory, (1989) or F. Ausubel et al., Current Protocols In Molecular Biology, Greene Publishing and Wiley-Interscience, New York (1987), the contents of each of which are herein incorporated by reference in their entirety. Suitable methods for synthesizing oligonucleotide probes are also described in Caruthers, Science, 230:281-285, (1985), the contents of which are incorporated by reference.

In an embodiment, nucleic acid template molecules are attached to a substrate (also referred to herein as a surface) and subjected to analysis by single molecule sequencing as described herein. Nucleic acid template molecules are attached to the surface such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mol. Bio. Rep. 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

In some embodiments, a plurality of nucleic acid molecules being sequenced is bound to a solid support. To immobilize the nucleic acid on a solid support, a capture sequence/universal priming site can be added at the 3' and/or 5' end of the template. The nucleic acids may be bound to the solid support by hybridizing the capture sequence to a complementary sequence covalently attached to the solid support. The capture sequence (also referred to as a universal capture sequence) is a nucleic acid sequence complimentary to a sequence attached to a solid support that may dually serve as a universal primer. In some embodiments, the capture sequence is polyNn, wherein N is U, A, T, G, or C, e g., 20-70, 40-60, e.g., about 50. For example, the capture sequence could be polyT40-50 or its complement. As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair.

In some embodiments, a barcode sequence is attached to the nucleic acid. See for example, Steinman et al. (PCT internal application number PCT/US09/64001), the content of which is incorporated by reference herein in its entirety.

EXAMPLE

Figure 8:
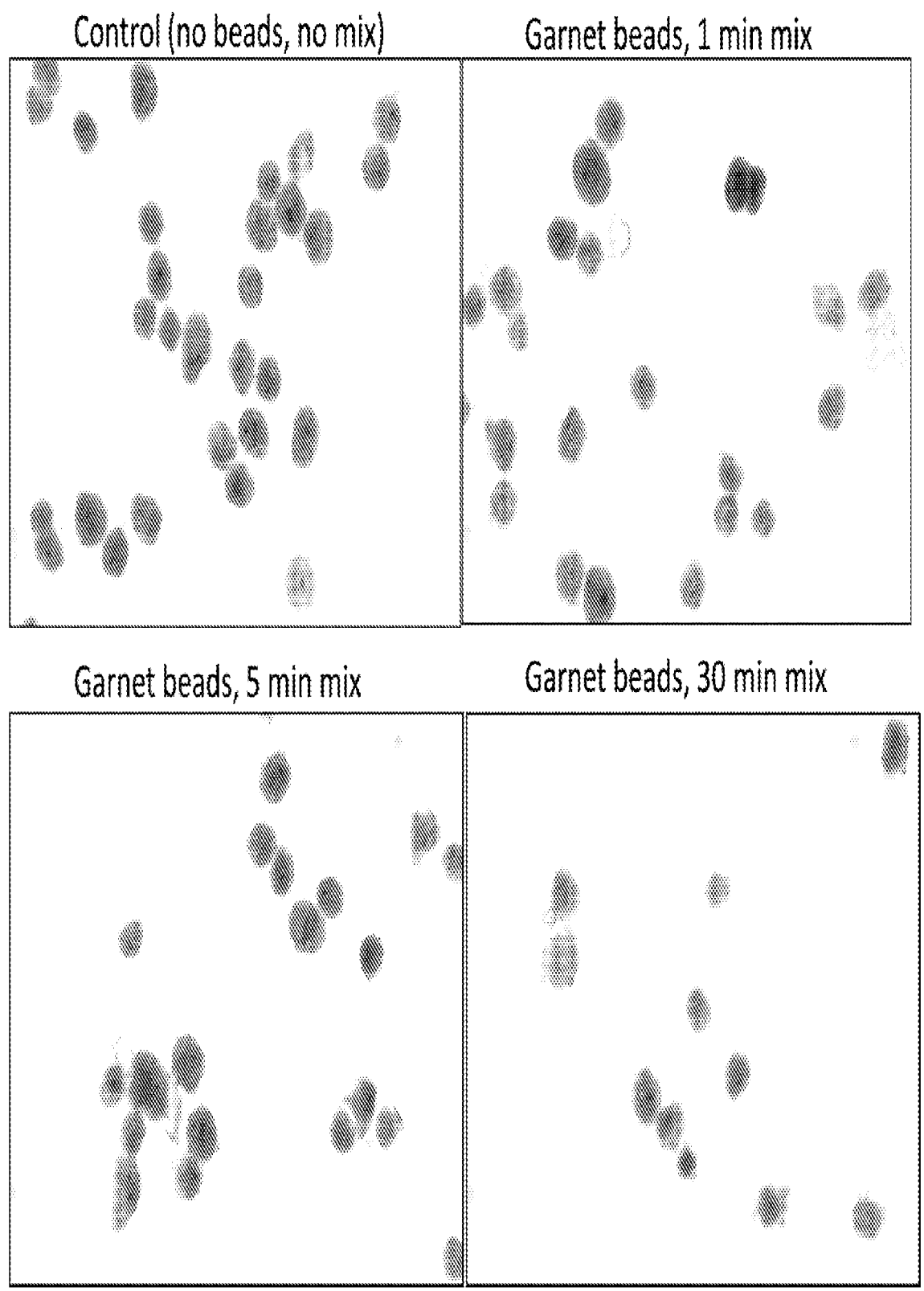
FIG. 8 shows a 40× view of cells exposed to various mix times with garnet beads.

FIG. 8 shows a 40× view of cells exposed to various mix times with garnet beads. The cells were the product of a test of embodiments of the bead beating protocol. Cell-line based ThinPrep® specimens were created using cultured CaSki cells (a cell line containing HPV-16 and sequences related to HPV-18) at a concentration of 100,000 cells/mL. Garnet beads (MO-BIO P/N 13123-05) were added to each 20 mL sample, and the samples were subjected to varying mix times on a platform vortexer.

Slides were prepared and cells were stained using the ThinPrep staining set, including nuclear stain, rinse solution, Orange G Solution, counter stain solution, and bluing solution. The slides were then cover-slipped and processed on a ThinPrep® 5000 Processor.

Surprisingly, the presence of garnet beads did not interfere with slide processing on the machine, nor did it inhibit viewing and analyzing the processed slides. Samples with and without beads each yielded similar processing metrics, meaning that the beads did not interfere with the function of the processor. Samples with and without beads also had similar slide cellularity and cell presentation.

Samples that were subjected to long mix times did experience a higher degree of filter occlusion and a decreased number of pulse-aspirations needed to achieve the target reduction in filter flow rate, which triggers the processor to stop drawing sample onto the filter. This effect also resulted in slides with decreased cellularity. This effect was only noticeable at mix times of 5 minutes or more.

The images of FIG. 8 are representative only of cell presentation, not overall slide cellularity, because the reviewer selected cellular areas of the slides to photograph. The cell presentation shows that there is not a significant cell morphology effect as a result of the presence of garnet beads or the mix time. Nuclear definition and stain quality are similar between all control and test parameters. There was only a small increase in cellular debris on the slides as a result of increased mixing.

The results of the experiment showed that increased lysis times resulted in lower cell counts, visual evidence of cellular debris in the sample, higher sample turbidity, increased lysate absorbance and increased ThinPrep® filter occlusion. The lysing did not however appear to affect the cell transfer or the quality of cell presentation on ThinPrep® slides.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of cervical screening, said method comprising:
providing a preserved biological sample comprising cells from the cervix and/or the endocervical canal of a subject;
partially lysing the preserved biological sample to create a mixture comprising lysed cells, whole cells, and molecular components;
performing a cytopathology assay on the whole cells in a first portion of the mixture; and
assaying a second portion of the mixture for the molecular components.

2. The method of claim 1, wherein the molecular components comprise components of one or more pathogens present in the biological sample and/or biomarkers correlated with an elevated risk of cancer.

3. The method of claim 2, wherein the one or more pathogens are selected from a group including, human papillomavirus (HPV), chlamydia, gonorrhea, trichomoniasis, and candidiasis.

4. The method of claim 2, wherein the one or more pathogens include bacteria, viruses, and/or yeast.

5. The method of claim 2, wherein assaying comprises genetic screening and the biomarkers correlated with an elevated risk of cancer are nucleic acids.

6. The method of claim 5, wherein genetic screening includes detecting the nucleic acids, quantifying the nucleic acids, the identifying nucleic acids, and/or sequencing the nucleic acids.

7. The method of claim 6, wherein the biomarkers are correlated with an increased risk of vaginal cancer and/or cervical cancer.

8. The method of claim 7, wherein the biomarkers include nucleic acid base pair changes associated with high-risk HPV types.

9. The method of claim 8, wherein the high-risk HPV types include HPV-6, HPV-11, HPV-16, HPV-18, HPV-31, HPV-33, HPV-35, HPV-39, HPV-45, HPV-51, HPV-52, HPV-56, HPV-58, HPV-68, HPV-73, and/or HPV-82.

10. The method of claim 9, wherein the high-risk HPV types include HPV-16, HPV-18, and/or HPV-45.

11. The method of claim 7, wherein the biomarkers include virus oncogene E6 and/or virus oncogene E7.

12. The method of claim 11, wherein the biomarkers include virus oncogene E6 mRNA and/or virus oncogene E7 mRNA.

13. The method of claim 7, wherein the biomarkers include SC6, SIX1, human cervical cancer 2 protooncogene (HCCR-2), P27, virus oncogene E6, virus oncogene E7, p16INK4A, Mcm proteins, Cdc proteins, topoisomerase 2 alpha, PCNA, Ki-67, Cyclin E, p-53, PAII, DAP-kinase, ESR1, APC, TIMP-3, RAR-β, CALCA, TSLC1, TIMP-2, DcR1, CUDR, DcR2, BRCA1, p15, MSH2, Rassf1A, MLH1, MGMT, SOX1, PAX1, LMX1A, NKX6-1, WT1, ONECUT1, SPAG9, Rb (retinoblastoma) proteins, pRb2/p130, and/or Bcl-2.

14. The method of claim 7, wherein the cytopathology assay comprises screening cells in the first portion of the mixture for squamous cell abnormalities or glandular cell abnormalities.

15. The method of claim 1, wherein the method further comprises obtaining cells from the cervix and/or endocervical canal of a subject, and contacting the cells with a preservative to create a preserved biological sample.

16. The method of claim 15, wherein the cells are obtained using a brush, spatula, swab, or syringe.

17. The method of claim 1, wherein partially lysing comprises mechanical shearing, detergent lysing, osmotic lysing, chemical denaturing, centrifuging, sonicating, freeze-thawing, or a combination thereof.

18. The method of claim 17, wherein mechanical shearing comprises syringe shearing, bead beating, or a combination thereof.

19. The method of claim 1, wherein an imager is used in the cytopathology assay and the imager identifies whole cells in the first portion of the mixture with the largest and darkest nuclei in the first portion.

20. A method of cervical screening, said method comprising:
providing a preserved biological sample comprising cells from the cervix and/or the endocervical canal of a subject;
partially lysing the preserved biological sample to create a mixture comprising lysed cells, whole cells, and molecular components;
performing a cytopathology assay on the whole cells in a first portion of the mixture; and
assaying a second portion of the mixture for molecular components associated with HPV.

* * * * *